US010292634B2

(12) United States Patent
Kan

(10) Patent No.: US 10,292,634 B2
(45) Date of Patent: May 21, 2019

(54) DEPTH-ADJUST MECHANISM FOR LANCING DEVICE

(71) Applicant: FACET TECHNOLOGIES, LLC, Kennesaw, GA (US)

(72) Inventor: Gil Kan, Alpharetta, GA (US)

(73) Assignee: FACET TECHNOLOGIES, LLC, Atlanta, GA (US)

( * ) Notice: Subject to any disclaimer, the term of this patent is extended or adjusted under 35 U.S.C. 154(b) by 210 days.

(21) Appl. No.: 14/036,154

(22) Filed: Sep. 25, 2013

(65) Prior Publication Data
US 2014/0088633 A1 Mar. 27, 2014

Related U.S. Application Data

(60) Provisional application No. 61/706,409, filed on Sep. 27, 2012.

(51) Int. Cl.
*A61B 5/151* (2006.01)
*A61B 5/15* (2006.01)

(52) U.S. Cl.
CPC ........ *A61B 5/15126* (2013.01); *A61B 5/1519* (2013.01); *A61B 5/15019* (2013.01);
(Continued)

(58) Field of Classification Search
CPC ........ A61B 5/150175; A61B 5/150183; A61B 5/15019; A61B 5/150198;
(Continued)

(56) References Cited

U.S. PATENT DOCUMENTS 4,203,446 A * 5/1980 Hofert .............. A61B 5/150022
173/114
4,660,570 A * 4/1987 Dombrowski ... A61B 5/150015
600/578
(Continued)

FOREIGN PATENT DOCUMENTS

DE 202012102771 U1 10/2012
EP 0565970 A1 * 10/1993 ........... A61B 5/1411
(Continued)

OTHER PUBLICATIONS

International Search Report and Written Opinion for PCT/US2013/061543; dated Dec. 20, 2013; 9 pgs.

*Primary Examiner* — Darwin P Erezo
*Assistant Examiner* — Erin L Colello
(74) *Attorney, Agent, or Firm* — Gardner Groff Greenwald & Villanueva, PC

(57) ABSTRACT

A lancing device with a depth-adjustment mechanism including an adjustably-positioned stop surface, a movable control member operably coupled thereto, and a resiliently deflectable leg that engages the stop surface and a lancet carrier to provide a soft stop for the lancet carrier. The lancet carrier deflects the leg in a forward phase of the lancing stroke, and then the leg contacts the stop surface to stop the forward motion of the lancet carrier at an extended lancing position. The stop surface can be adjustably positioned so that different portions thereof are engaged to stop the lancet carrier at deeper or shallower positions. In example embodiments, the depth-adjustment mechanism includes a rotary dial and an extension arm of the leg, with the dial including a rotary wheel and a rotary shaft extending axially therefrom, the wheel forming the movable adjustment member, and the shaft forming the adjustably positioned stop surface.

14 Claims, 7 Drawing Sheets

(52) U.S. Cl.
CPC .... *A61B 5/150022* (2013.01); *A61B 5/15111* (2013.01); *A61B 5/15117* (2013.01); *A61B 5/150152* (2013.01); *A61B 5/15194* (2013.01); *A61B 5/150412* (2013.01); *A61B 5/150503* (2013.01); *A61B 5/1513* (2013.01); *A61B 5/150167* (2013.01)

(58) Field of Classification Search
CPC .......... A61B 5/150458; A61B 5/15115; A61B 5/15117; A61B 5/15126; A61B 5/15128; A61B 5/1513; A61B 5/15144; A61B 5/1519; A61B 5/15192; A61B 5/15194–5/15198; A61B 5/1411; A61B 5/15142; A61B 5/15186; A61B 5/15146; A61B 5/15188; A61B 5/1444; A61B 5/1433; A61B 5/150053; A61B 5/150068; A61B 5/150106; A61B 5/15016; A61B 5/150167; A61B 5/15029; A61B 5/150297; A61B 5/150549; A61B 5/15107; A61B 5/15109; A61B 5/15111; A61B 5/15113

See application file for complete search history.

(56) References Cited

U.S. PATENT DOCUMENTS

| | | | | |
|---|---|---|---|---|
| 4,735,203 A * | 4/1988 | Ryder | ................ | A61B 5/15142 606/182 |
| 4,924,879 A * | 5/1990 | O'Brien | ................ | A61B 5/1411 600/583 |
| 5,318,583 A * | 6/1994 | Rabenau | ............ | A61B 5/15186 606/182 |
| 5,527,334 A * | 6/1996 | Kanner | ............... | A61B 5/15142 600/583 |
| 5,730,753 A * | 3/1998 | Morita | .............. | A61B 5/150022 600/583 |
| 5,772,677 A * | 6/1998 | Mawhirt | .......... | A61B 17/32093 606/181 |
| 5,797,940 A * | 8/1998 | Mawhirt | .......... | A61B 17/32093 606/167 |
| 5,984,940 A * | 11/1999 | Davis | ................ | A61B 5/15186 606/181 |
| 6,015,392 A * | 1/2000 | Douglas | ............. | A61B 5/14532 600/573 |
| 6,045,567 A | 4/2000 | Taylor et al. | | |
| 6,322,574 B1 | 11/2001 | Lloyd et al. | | |
| 6,358,265 B1 * | 3/2002 | Thorne, Jr. | ........ | A61B 5/15142 606/181 |
| 7,481,819 B2 | 1/2009 | Koeppel et al. | | |
| 7,678,127 B2 * | 3/2010 | Trissel | ............. | A61B 5/150022 606/181 |
| 7,758,516 B2 * | 7/2010 | Perez | ................ | A61B 10/0045 600/583 |
| 7,867,244 B2 * | 1/2011 | Lathrop | ............... | A61B 5/1411 606/181 |
| 7,909,842 B2 * | 3/2011 | Flynn | ................... | A61B 5/1411 606/181 |
| 7,914,547 B2 * | 3/2011 | Curry | .................. | A61B 5/1411 606/181 |
| 7,955,348 B2 * | 6/2011 | Trissel | ................... | A61B 5/151 606/181 |
| 7,998,160 B2 * | 8/2011 | Lathrop | .......... | A61B 5/150022 606/181 |
| 8,016,848 B2 * | 9/2011 | Lathrop | ............... | A61B 5/1411 606/181 |
| 8,034,068 B2 * | 10/2011 | Koeppel | .......... | A61B 5/1411 606/181 |
| 8,398,664 B2 * | 3/2013 | Lamps | ................. | A61B 5/1411 606/181 |
| 8,449,480 B2 | 5/2013 | Fowler et al. | | |
| 9,724,031 B2 * | 8/2017 | Yi | ...................... | A61B 5/15128 |
| 9,724,034 B2 * | 8/2017 | Nicholls | ........... | A61B 5/15194 |
| 2004/0087990 A1 * | 5/2004 | Boecker | ............... | A61B 5/1411 606/181 |
| 2004/0098010 A1 * | 5/2004 | Davison | ............... | A61B 5/1411 606/181 |
| 2004/0260324 A1 * | 12/2004 | Fukuzawa | ........ | A61B 5/150022 606/181 |
| 2004/0267300 A1 * | 12/2004 | Mace | ................ | A61B 5/150022 606/182 |
| 2005/0149089 A1 * | 7/2005 | Trissel | ............ | A61B 5/150022 606/181 |
| 2005/0288699 A1 * | 12/2005 | Schraga | ........... | A61B 5/150022 606/181 |
| 2006/0129122 A1 * | 6/2006 | Wyrick | ............... | A61M 5/2033 604/506 |
| 2008/0027474 A1 * | 1/2008 | Curry | .............. | A61B 5/150022 606/181 |
| 2008/0077167 A1 * | 3/2008 | Flynn | ............. | A61B 5/150022 606/172 |
| 2008/0082117 A1 | 4/2008 | Ruf | | |
| 2009/0099586 A1 * | 4/2009 | Koeppel | ............... | A61B 5/1411 606/182 |
| 2010/0010528 A1 * | 1/2010 | Shi | ................... | A61B 5/150022 606/182 |
| 2010/0057119 A1 * | 3/2010 | Robbins | ............ | A61B 5/15146 606/182 |
| 2010/0094326 A1 * | 4/2010 | Robbins | ............ | A61B 5/15146 606/183 |
| 2010/0274273 A1 * | 10/2010 | Schraga | ............... | A61B 5/1411 606/172 |
| 2011/0130782 A1 * | 6/2011 | Kan | ..................... | A61B 5/1411 606/182 |

FOREIGN PATENT DOCUMENTS

| | | | | |
|---|---|---|---|---|
| EP | 1405595 A1 | 4/2004 | | |
| WO | 0128423 A2 | 4/2001 | | |
| WO | WO 03071940 A1 * | 9/2003 | .......... | A61B 5/1411 |
| WO | WO 2006004859 A2 * | 1/2006 | .......... | A61B 5/1411 |
| WO | 2006031535 A2 | 3/2006 | | |
| WO | WO 2008138443 A1 * | 11/2008 | .......... | A61B 5/1411 |
| WO | WO 2009037341 A1 * | 3/2009 | .......... | A61B 5/1411 |

* cited by examiner

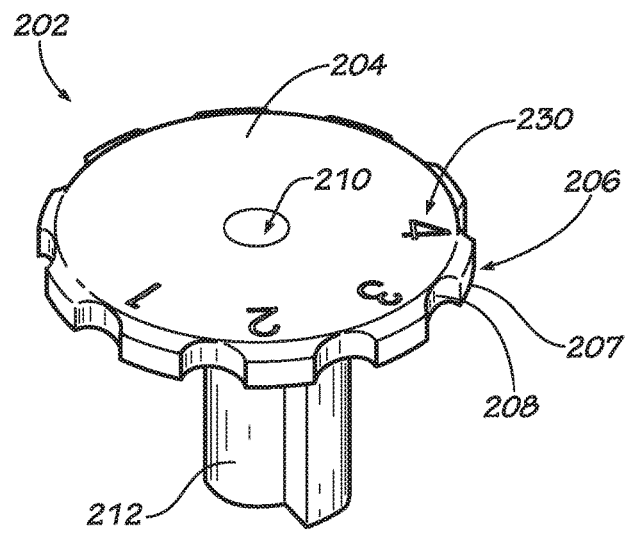
FIG. 4
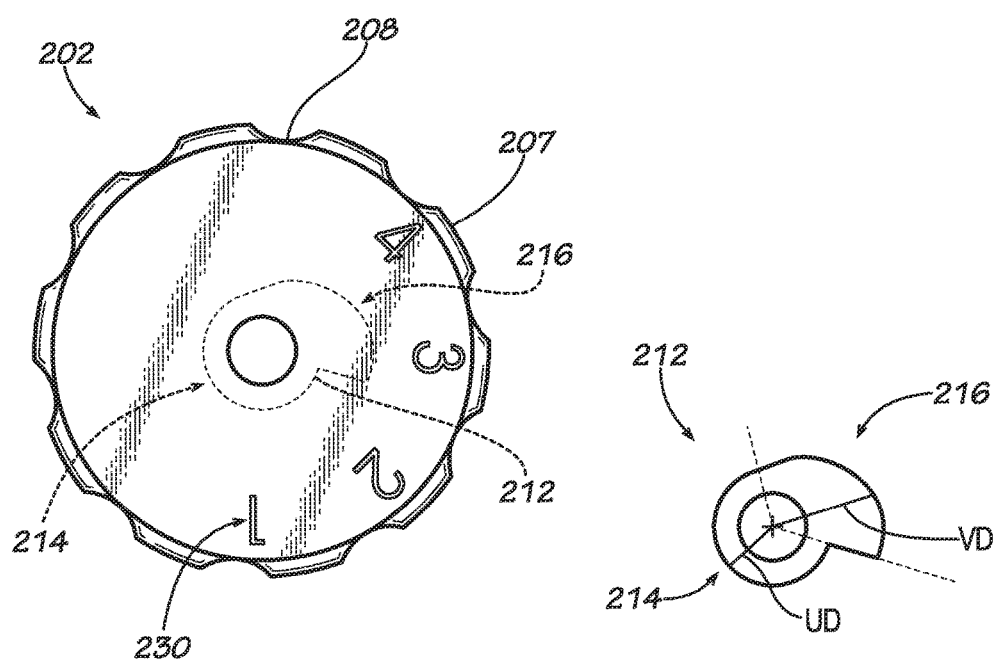
FIG. 5  FIG. 6

DEPTH-ADJUST MECHANISM FOR LANCING DEVICE

CROSS-REFERENCE TO RELATED APPLICATION

This application claims the priority benefit of U.S. Provisional Patent Application Ser. No. 61/706,409 filed Sep. 27, 2012, the entirety of which is hereby incorporated herein by reference for all purposes.

TECHNICAL FIELD

The present invention relates generally to the field of medical devices and procedures, and particularly to lancing devices with depth-adjustment mechanisms for adjusting the penetration depth of lancets.

BACKGROUND

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other biasing means of the drive mechanism, and a release mechanism for releasing the drive mechanism upon actuation. A lancet is typically propelled by the drive mechanism from a retracted position within the housing to an extended position wherein a sharp tip portion of the lancet projects from the housing to prick the subject's skin at a desired lancing site.

Lancing devices are available in multi-use and disposable designs. In multi-use designs, the lancet is a disposable component that is removably mounted into a receiver or lancet carrier of the drive mechanism. A used lancet is removed from the lancet carrier after sampling for subsequent disposal. An ejection mechanism can optionally be included for discharge of the used lancet from the lancing device. A new, sterile lancet is then replaced into the lancet carrier for further sampling. In disposable designs, the lancet and carrier are an integral part and the lancing device is disposed of after a single use.

A depth-adjustment mechanism can optionally be provided to adjust the penetration depth of the lancet, to control sample size and/or to minimize pain. Known depth-adjustment mechanisms include endcaps that are adjustably positioned relative to the lancing device housing, but they are generally susceptible to accidental and unknowing manipulation to a different depth setting, and they can be difficult to manipulate for people with limited dexterity. Other known depth-adjustment mechanisms include movable stops that limit the travel of the lancet by contact with the lancet carrier, but they generally increase the vibrations and impact force thereby causing more pain to the patient.

Accordingly, it can be seen that needs exist for improvements to depth-adjustment mechanisms for lancing devices. It is to the provision of improved lancing devices and lancing depth-adjustment mechanisms that the present invention is primarily directed.

SUMMARY

Generally described, the present invention relates to a lancing device including an improved depth-adjustment mechanism that provides a soft stop for a lancet carrier holding a lancet to reduce vibration and thereby provide a less-painful lancing experience to the patient. The depth-adjustment mechanism includes an adjustably-positioned stop surface, a movable control member operably coupled thereto, and a resiliently deflectable leg that engages the stop surface and the lancet carrier. The lancet carrier engages and deflects the leg in a forward phase of a lancing stroke, and then the deflecting leg engages the stop surface to stop the forward motion of the lancet carrier at an extended lancing position. The control member is adjustably positionable to move different portions of the stop surface into an engagement position where they are contacted by the leg to adjust the extended position and thereby adjust a penetration depth of the lancet to be deeper or shallower. In this way, the resiliently deflectable leg is operably interposed between the lancet carrier and the stop surface to produce a soft (non-instant) stop of the lancet carrier at the extended position to reduce vibration for a less painful lancing experience.

In an example embodiment, the depth-adjustment mechanism includes a rotary dial having a rotary wheel and a rotary shaft extending axially therefrom, with the wheel forming the movable adjustment member, and with the shaft including an eccentric surface forming the stop surface. The resiliently deflectable leg may be a part of a return spring that retracts the lancer carrier after it reaches the extended position, for example, the leg may include an extension arm that contacts the stop surface and is bent at an angle from the remainder of the return-spring leg.

In alternative embodiments, the adjustably-positioned stop surface is provided by a ramp that is linearly slidable to place different portions thereof in the engagement position to adjust the penetration depth of the lancet. In other alternative embodiments, the extension arm is resiliently deflectable with respect to the remainder of the leg to provide an even softer stop for the lancet carrier. And in other embodiments, the components of the depth-adjustment mechanism are configured in other arrangements to provide the same soft stop for the lancet carrier, as described herein.

In another aspect, the invention relates to a depth-adjustment mechanism as described herein for incorporation into a lancing device of the same or a different design as is described herein. And in yet another aspect, the invention relates to a depth-adjustment mechanism including the features described herein for providing the soft stop but without including the features described herein for providing the penetration-depth adjustability.

These and other aspects, features, and advantages of the invention will be understood with reference to the drawing figures and detailed description herein, and will be realized by means of the various elements and combinations particularly pointed out in the appended claims. It is to be understood that both the foregoing summary and the following brief description of the drawings and detailed description of example embodiments are explanatory of typical embodiments of the invention, and are not unnecessarily restrictive of the invention, as claimed.

BRIEF DESCRIPTION OF THE DRAWINGS

FIG. 4 is a top perspective view of a depth dial of the depth-adjustment mechanism of the lancing device of FIG. 1.

FIG. 5 is a top view of the depth dial of FIG. 4, showing a hidden eccentric stop surface in phantom lines.

FIG. 6 shows the eccentric stop surface of FIG. 5.

DETAILED DESCRIPTION OF EXAMPLE EMBODIMENTS

Figure 1:
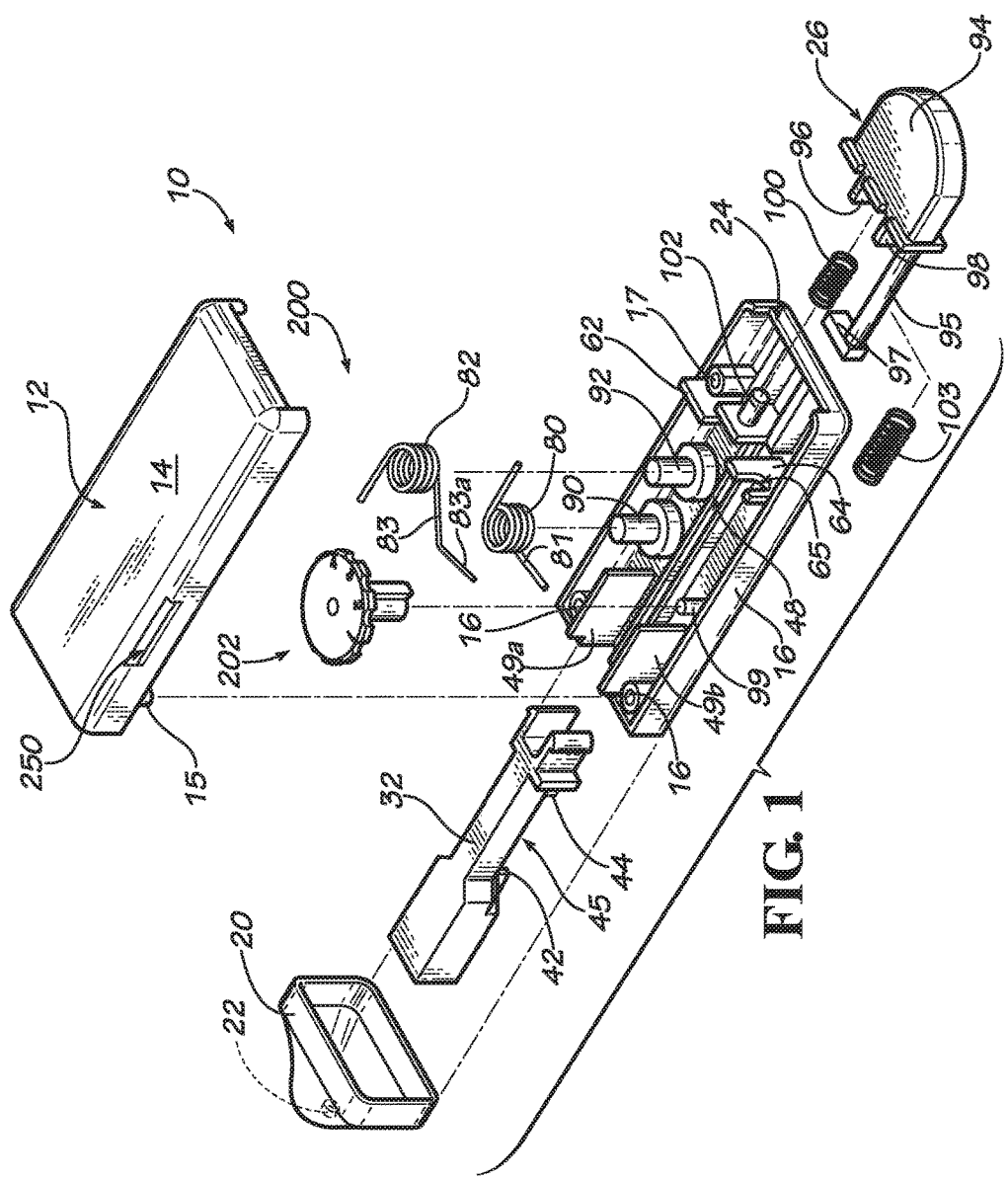
FIG. 1 is an exploded perspective view of a lancing device with a depth-adjustment mechanism according to an example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be unnecessarily limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-11 show a lancing device 10 with a depth-adjustment mechanism 200 according to an example embodiment of the present invention. The lancing device 10 includes a charging mechanism, a drive mechanism, a release mechanism, and a housing 12 for these components. The drive mechanism includes a lancet carrier 32 that carries a lancet 30 through a lancing stroke. The charging mechanism is operable to charge the drive mechanism, and the release mechanism is operable to release the lancet carrier to be driven by the charged drive mechanism to propel the lancet carrier (and thus the lancet) through the lancing stroke.

The details of the housing 12, lancet carrier 32, drive mechanism, charging mechanism, and release mechanism depicted and described herein are representative and not limiting of the invention. Thus, many other conventional housings, lancet carriers, drive mechanisms, charging mechanisms, and/or release mechanisms can be used with good results, as long as they do not interfere with the structures and functionality of the depth-adjustment mechanism, and as long as the drive mechanism (or another mechanism) includes cooperating features as needed to provide the functionality of the depth-adjustment mechanism. That is, the improved depth-adjustment mechanism 200 described and illustrated herein can be incorporated into many other lancing-device designs.

In the depicted embodiment, the housing 12, lancet carrier 32, drive mechanism, charging mechanism, and release mechanism of the lancing device 10 are substantially similar to those of U.S. Pat. No. 8,034,068, which is hereby incorporated by reference as though fully set forth herein. Thus, repetitive explanation herein will be kept to a minimum while still fully describing the lancing device 10. For convenience, many of the reference characters used herein have been selected to match those of U.S. Pat. No. 8,034,068 for common parts. In other embodiments, other designs of lancing devices, with other charge, drive, and/or release mechanisms, can be used with the depth-adjustment mechanism 200 of the present invention. For example, while the depicted lancing device 10 is a multi-use device, in other embodiments the depth-adjustment mechanism 200 is incorporated into a disposable lancing device. And while the depicted lancing device 10 includes a single mechanism for both charging and releasing the drive mechanism, in other embodiments separate charging and release mechanisms are provided.

Figure 2:
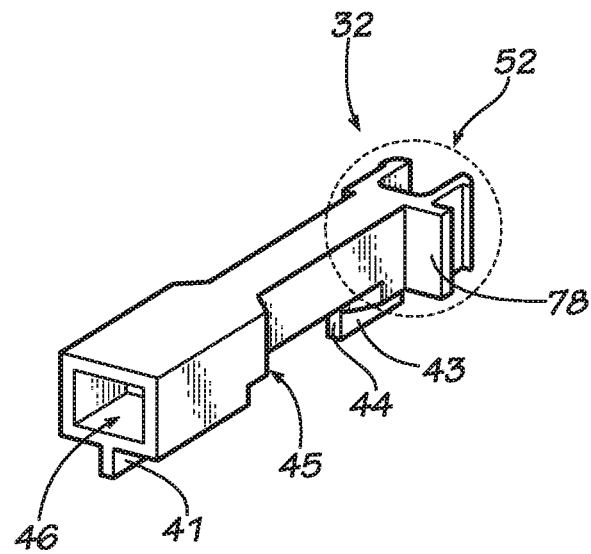
FIG. 2 is a front perspective view of a lancet carrier of the lancing device of FIG. 1.
Figure 3:
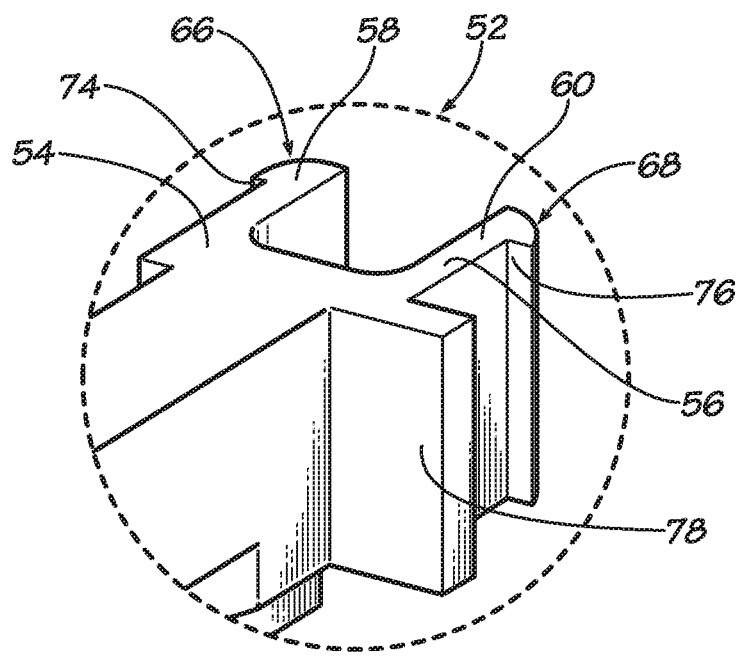
FIG. 3 is a detailed perspective view of the distal end of the lancet carrier of FIG. 2.

Referring primarily to FIGS. 1-3, the depicted lancing device 10 includes a housing 12 defining an axial bore through which the lancet carrier travels along its lancing stroke. The depicted housing 12 has a top portion 14 connected to a bottom portion 16 by one or more inter-engaging surface features. For example, crush pins 15 extending from the top housing 14 can be received in conduits 17 formed within the bottom housing 16 to permanently or removably couple the housing portions together. In other embodiments, adhesives are used to couple the housing portions together, and/or the housing is formed in other configurations.

Figure 10:
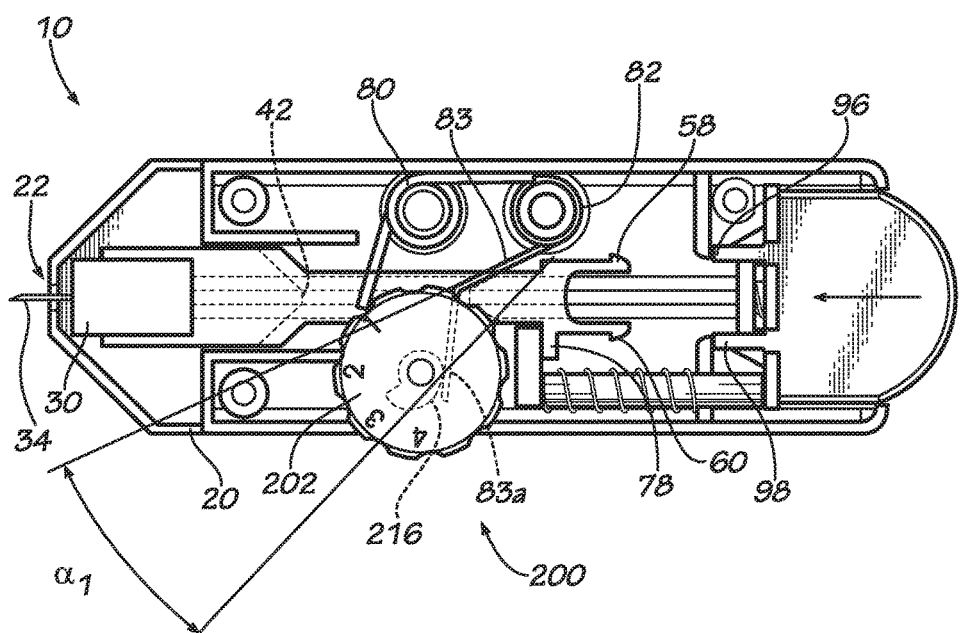
FIG. 10 shows the lancing device of FIG. 7 in an actuated position, with the depth-adjustment mechanism configured for maximum depth of penetration.
Figure 11:
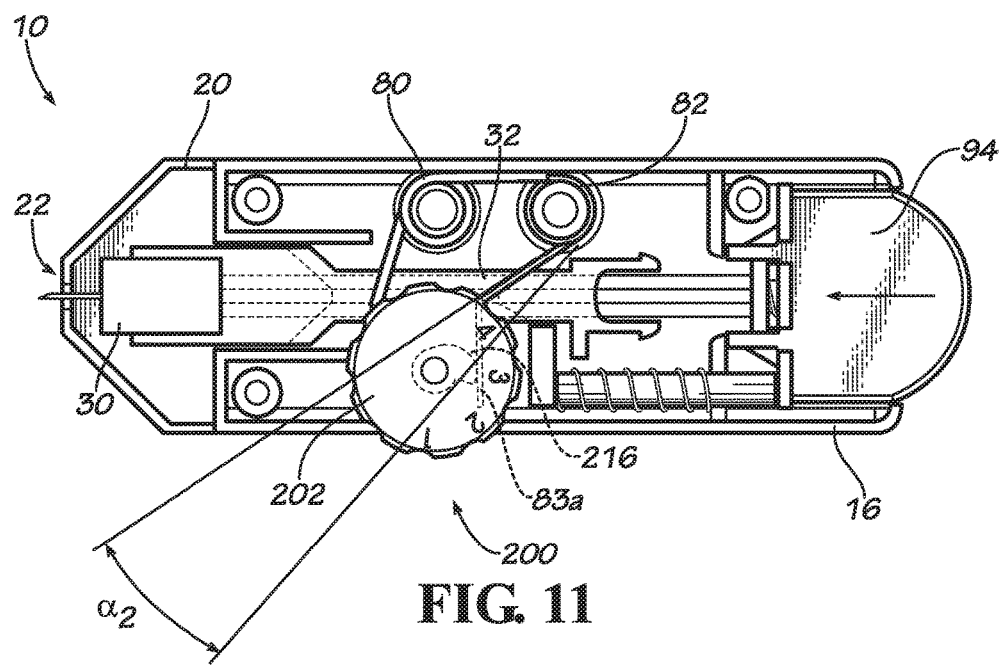
FIG. 11 shows the lancing device of FIG. 7 in an actuated position, with the depth-adjustment mechanism positioned for minimum depth of penetration.

The housing 12 includes a lancing opening 22 at its forward end through which a sharp tip 34 of the lancet 30 extends externally in an extended position of the lancing stroke to penetrate the skin of a subject at a lancing site (see FIGS. 10-11). The housing 12 typically includes an endcap 20 removably connected to its forward end so that a used lancet 30 can be manually removed from the lancing device 10 and a fresh lancet can be manually inserted into the device in its place for use. Thus, the lancing opening 22 can be formed in the endcap 20, as depicted. At the rearward end of the housing 12 opposite the endcap 20 is an opening 24 for receiving a charging/release actuator assembly 26 and for guiding the same along a predefined axial path of travel.

Figure 7:
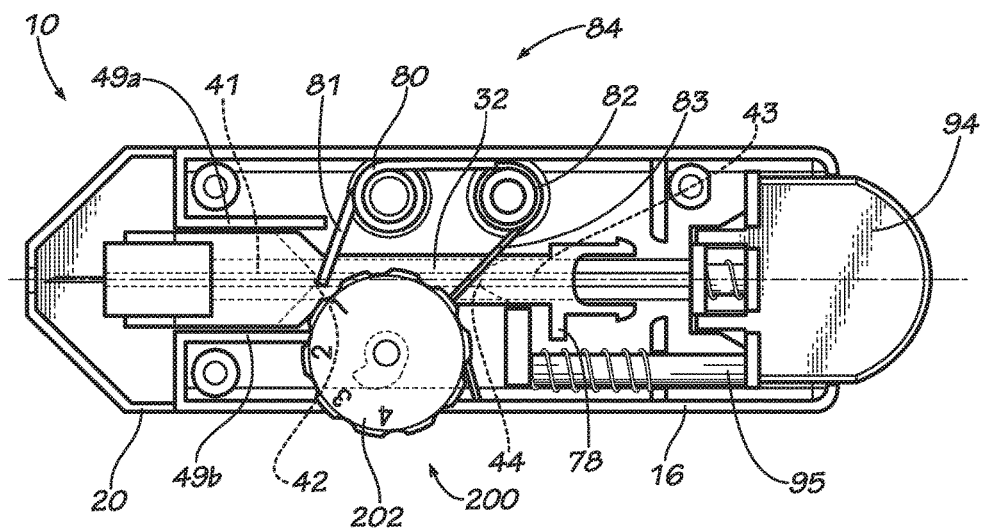
FIG. 7 is a top longitudinal cross-sectional view of the lancing device of FIG. 1 in a neutral position.
Figure 8:
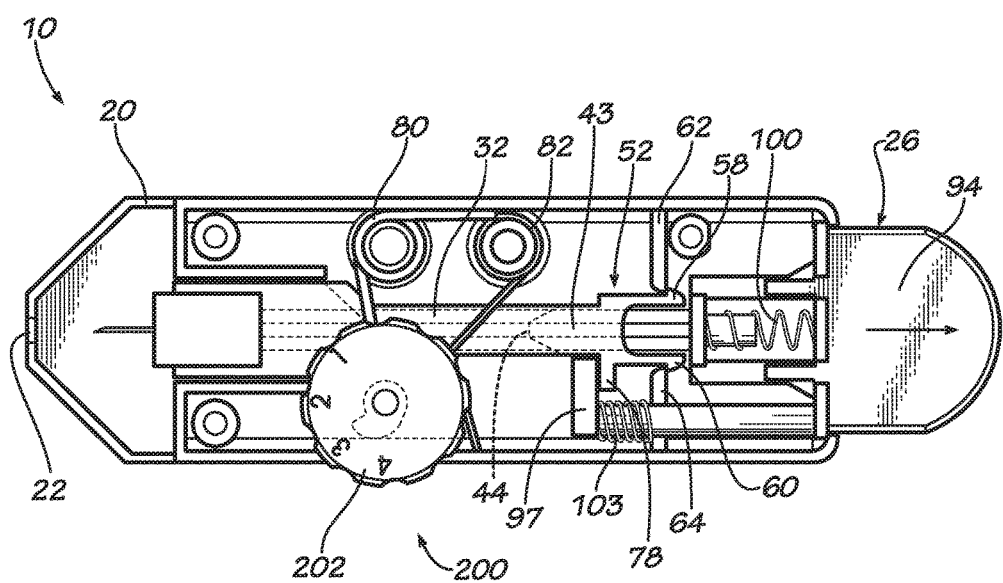
FIG. 8 shows the lancing device of FIG. 7 in a charged position.

The lancet carrier 32 of the drive mechanism includes at least one guide element and the housing 12 includes at least one guide element that engage each other such that the movement of the lancet carrier through the lancing stroke defines a linear stroke axis (see axial centerline in FIG. 7). In the depicted embodiment, the lancet carrier 32 includes two male guide elements, such as a forward/proximal guide arm 41 and a rear/distal guide arm 43 extending from a lower surface of the lancet carrier 32. And the female guide element includes a guide channel 48 formed in the bottom housing portion 16 and slidingly receiving the guide arms 41, 43 to linearly guide the lancet carrier 32 along the lancing stroke axis. Additionally or alternatively, laterally offset walls 49a, 49b can be provided on the bottom housing portion 16 to receive the lancet carrier 32 therebetween and linearly guide the lancet carrier 32 as traverses along the lancing stroke axis. In other embodiments, other inter-engaging guide elements are provided to promote linear relative translation (and prevent relative rotation or lateral movement) between these two parts (e.g., channels on the lancet carrier that engage at least one rib within the housing, or other mating guide elements).

The lancet carrier 32 defines drive and return contact surfaces that are engaged by cooperating features of the drive mechanism to advance and retract it through the lancing stroke. In the depicted embodiment, the guide elements 41, 43 of the lancet carrier 32 are spaced apart and include respective drive and return contact surfaces 42, 44 that generally face each other, are generally transverse to the lancing stroke axis, and cooperatively define therebetween a control opening 45. The drive and return contact surfaces 42, 44 are engaged by other elements of the drive mechanism (which are received in the control opening 45) to control the lancet carrier 32 during the forward and return phases of the lancing stroke, as described below.

In addition, the lancet carrier 32 includes a lancet mount at its forward end and charging and release features at its rearward end. In the depicted embodiment, the lancet mount is provided by an opening 46 that is sized and shaped to securely but releasably receive and hold the replaceable lancet 30 during use. The depicted charging features include a U-shaped portion 52 of the lancet carrier 32 that inter-engages the charging/release actuator assembly 26, with these portions of the lancing device 10 being substantially similar to those of U.S. Pat. No. 8,034,068. Further details of the lancet carrier's charge/release features and their interaction with the charging/release mechanism will now be described before completing the description of the drive mechanism.

In the depicted embodiment, the U-shaped portion 52 of the lancet carrier 32 includes two axially-rearward extending arms 54, 56 and a fin 78 that projects generally laterally from one of the arms. The charge/release actuator assembly 26 includes a push/pull button 94, a leg 95 extending axially from the button, and a foot 97 extending laterally from the leg that engages the fin 78 of the lancet carrier 32 when the push/pull button is retracted. As such, retraction of the push/pull button 94 retracts the lancet carrier 32 against a forward-biasing force of the drive mechanism to a charged position where transverse catch surfaces 74, 76 of chamfered barbs 58, 60 of the arms 54, 56 of the U-shaped portion 52 engage cooperating locking tabs 62, 64 of the housing 12 (see FIG. 8).

In addition, the push/pull button 94 includes trigger posts 96, 98 extending axially forward therefrom for engaging chamfer surfaces 66, 68 of the chamfered barbs 58, 60 to release the lancet carrier 32 in the charged position to be propelled under the influence of the drive mechanism. As such, in the depicted embodiment the push/pull button 94 of the actuator assembly 26 functions as the user interface for both charging and releasing the lancing device 10, with the features of the charging mechanism and the release mechanism combined into a single mechanism for both functions. It will be readily understood by persons of ordinary skill in the art how to provide other embodiments with separate charging and release actuators.

Figure 9:
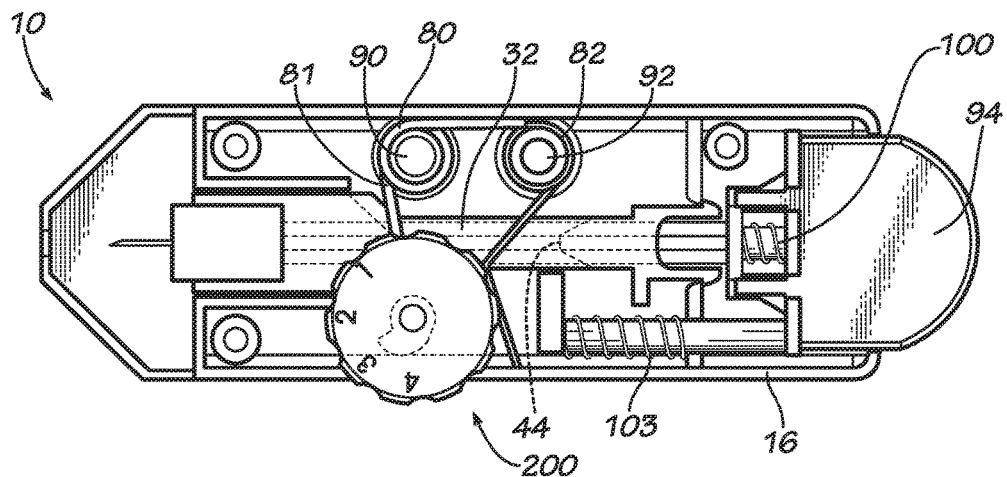
FIG. 9 shows the lancing device of FIG. 7 in a charged and ready position.

The depicted charging mechanism further includes one or more equilibrium springs that induce the push/pull button 94 into a charged and ready position (see FIG. 9). In the depicted embodiment, a push-resist spring 100 and an oppositely opposed pull-resist spring 103 cause the push/pull button 94 to move to an equilibrium position wherein the springs 100, 103 counter-balance one another after the push/pull button is retracted to its extended position and released (see FIG. 9). The push-resist spring 100 can be a coil compression spring mounted on a spring post 102 of the housing 12 and biased between a transverse rearward wall of the housing 12 and a central portion of a transverse forward wall of the push/pull button 94. For example, the central portion of the push/pull button 94 can be defined between its trigger posts 96, 98 and can include an orifice (not shown) formed therein such that a portion of the pull-resist spring 100 is retained therein. And the pull-resist spring 103 can be a coil compression spring mounted on the charging-button leg 95 and biased between the charging-button foot portion 97 and the locking tab 64 of the housing 12. In other embodiments, the lancing device includes other conventional structures operable to manipulate the lancet carrier to charge the drive mechanism, for example, with no or different equilibrium-inducing spring arrangements, with other inter-engaging features of the lancet carrier and charge/release mechanism, and/or with separate charge and release actuators.

Continuing now with the drive mechanism, at least one spring element is provided for driving the lancet carrier 32 through the forward and return phases of the lancing stroke. In the depicted embodiment, there are two torsion springs, a drive spring 80 and a return spring 82, that cooperate to drive and return the lancet carrier 32 through the lancing stroke. The drive and return torsion springs 80, 82 include at least one respective leg extending therefrom into the control opening 45 for engagement with the respective drive and return contact surfaces 42, 44 of the guidance elements 41, 43 of the lancet carrier 32. That is, the leg 81 of the drive spring 80 engages the drive contact surface 42 of the proximal drive element 41, and the leg 83 of the return spring 82 engages the return contact surface 44 of the distal return element 43 (see FIGS. 7-11). By this engagement, the drive spring 80 drives the lancet 30 on the lancet carrier 32 from its charged position to its extended position to lance the skin, and the return spring 82 retracts the lancet from its extended position back into the housing 12 after lancing the skin. In the depicted embodiment, the return spring 82 also serves to provide depth adjustment to the lancet 30 by cooperating with the depth-adjustment mechanism 200, as described below.

Typically, the drive and return springs 80, 82 are generally similar in shape and form, except with the drive spring being the stronger of the two springs. The drive torsion spring 80 can be mounted to the housing 12 on a first axle or pivot 90, and the return torsion spring 82 mounted on a second axle or pivot 92, with an inner wall of the housing from which the pivots extend serving as a retainer for the springs. The axles 90, 92 can be offset laterally from the lancing stroke axis and spaced apart relative to the lancing stroke axis, or they can be configured in other ways to provide the same drive and return functionality.

In other embodiments, the return spring is provided by another type of spring element that has a resilient extension leg that engages the drive mechanism (e.g., a leaf or cantilever spring, a compression or tension coil spring that is axially resilient and includes a transverse resilient extension leg, or another resilient member including a resilient extension leg) and also engages the depth-adjustment mechanism 200 to provide the depth-adjustment functionality described herein. In yet other embodiments, the drive and return functionality is provided by a single spring element (e.g., a coil spring, torsion spring, leaf/cantilever spring, or other resilient member) that includes a resilient extension leg that engages the drive mechanism and also engages the depth-adjustment mechanism 200 to provide the depth-adjustment functionality described herein. And in still other embodiments, a separate drive spring is provided by any other conventional type of spring element (e.g., a compression or tension coil spring, leaf or cantilever spring, or other resilient member), regardless of the type of return spring provided.

Referring primarily to FIGS. 4-6, details of the depth-adjustment mechanism 200 will now be described. The depth-adjustment mechanism 200 provides adjustment to the depth of penetration of the lancet 30 in the skin when the lancet is in the extended position of the lancing stroke. Generally described, the depth-adjustment mechanism 200 includes an adjustably positioned stop surface and a resiliently deflectable leg associated with a movable adjustment control member and a return spring of the drive mechanism (respectively or non-respectively). The lancet carrier 32 (or another element of the drive mechanism) engages and angularly deflects the resiliently deflectable leg in the forward phase of the lancing stroke of the lancet carrier, then the leg (or an extension thereof) engages the stop surface to stop the forward motion of the lancet carrier at the extended position, and then the return spring retracts the lancet carrier back into the housing 12.

In the depicted embodiment, the depth-adjustment mechanism 200 includes a rotary depth dial 202 having a movable adjustment control member in the form of a rotary wheel 204 and a rotary shaft 212 extending axially downward therefrom, with the adjustably positioned stop surface in the form of an eccentric stop surface 216 formed on the shaft. To provide for rotational adjustment of the wheel 204 and the eccentric stop surface 216, the depth dial 202 is rotationally mounted to the housing 12. In the depicted embodiment, the rotary shaft 212 includes an axially extending opening 210 that rotatably mounts to a pin 99 extending from the housing 12. In other embodiments, other rotational mounting arrangements can be used, for example these rotational-mounting features can be reversed.

The depicted depth wheel 204 is generally disc-shaped (or at least a portion of it is) and includes a peripheral portion 206 for manually gripping by the user to rotate the wheel and thereby rotate the eccentric stop surface 216 to the desired depth-setting position. For example, the peripheral portion 206 of the wheel 204 can include a series of alternating surfaces, for example, outwardly knurled portions 207 and inwardly knurled portions 208 therebetween, to provide enhanced grasping capabilities for users, especially those with reduced or limited dexterity. In addition, indicia such as markings 230 can be provided around the depth wheel 202 corresponding to positions of the eccentric stop surface 216 to indicate the depth of penetration provided by the depth dial 202. The depth-wheel 204 is positioned so that it is accessible for actuation by a user, for example it can extend partially out of the housing 12 through an opening 250 for gripping and actuation by the user. The depth wheel 204 can be rotated to individually position each of the depth indicia 230 (e.g., numerals 1-4) in a setting position (e.g., extending through the opening 250 and thus visible to the user) to form different depth settings. In other embodiments, the wheel can have no or other conventional gripping features and/or indicia to provide none of or the same functionality.

The adjustably-positionable eccentric stop surface 216 (of the rotary shaft 212 of the depth dial 202) is positioned within the housing 12 for inter-operation with the lancet carrier 32. The eccentric stop surface 216 has a non-uniform radius so that it provides a series of portions with increasingly larger or smaller radiuses. The eccentric stop surface 216 can be a smooth surface (as depicted), it can have a stepped configuration (e.g., with discrete indexed positions), it can be formed by a series of outwardly (from the shaft) or downwardly (from the wheel) extending tabs or protrusions, and/or it can be provided in other configurations for cooperating with the return spring 82 to provide variable lancet-depth adjustment. Typically, the eccentric stop surface 216 does not extend peripherally all the way around the shaft 212, in which case the shaft also includes a peripheral surface portion 214 that is not used as a stop surface, and this surface portion can have a generally uniform radius, as depicted.

In the depicted embodiment, the eccentric stop surface 216 defines a peripheral profile radiused from a central point of the rotary shaft 212 (see center mark of FIG. 6) outward to the periphery of the shaft. For example, a variable radial dimension VD can be defined along the eccentric stop surface 216 (e.g., about 130 degrees of the total 360 degrees periphery), and a uniform radial dimension UD can be defined along the uniform shaft portion 214 (e.g., the remaining about 230 degrees). Thus, the rotary shaft 212 has a progressively increased (or decreased) radius and thus thickness that forms the eccentric stop surface 216.

The depth of penetration of the sharp tip 34 of the lancet 30 is adjusted by adjusting the angular position of the depth dial 202. Different angular positions of the depth dial 202 position the eccentric stop surface 216 with different of its portions in the engagement position (facing rearward in the depicted embodiment and in another direction in other embodiments) for engagement by the return-spring extension arm 83a. That is, the depth dial 202 is rotatably mounted such that its angular position determines which portion of the eccentric stop surface 216 faces rearward and thus will be engaged by the extension arm 83a of the return spring 82 as it is deflected by the lancet carrier 32 advancing along the lancing stroke.

The return contact surface 44 of the lancet carrier 32 contacts the leg 83 of the return spring 82 when the lancet carrier is propelled forward from the charged position to the extended position. After contact occurs, the further advancing lancet carrier 32 causes the return-spring leg 83 to angularly deflect, which causes the return-spring extension arm 83a to angularly displace. The return-spring extension arm 83a displaces until it contacts the eccentric stop surface 216, which stops its movement, which in turn stops the movement of the return-spring leg 83, which in turn stops the movement of the lancet carrier 32, thereby defining its extended position. In this way, the eccentric stop surface 216 is rammed into not by a rigid member of the lancet carrier, but instead by the resiliently deflectable return spring 82.

The indicia 230 of the depth wheel 204 correspond respectively to different portions of the eccentric stop surface 216 so that positioning each of the indicia in a setting position places the corresponding stop-surface portion in the engagement position to stop the forward motion of the lancet carrier 32 along the lancing stroke. For example, in FIG. 10 the angular position of the eccentric stop surface 216 (as determined by the angular position of the depth wheel 204) provides a maximum depth of lancet penetration, because the rearward-facing portion of the stop surface is farthest forward so that return-spring extension arm 83a contacts it after the lancet carrier has traveled farthest. But in FIG. 11, the angular position of the eccentric stop surface 216 provides a minimum depth of lancet penetration, because the rearward-facing portion of the stop surface is farthest rearward so that return-spring extension arm 83a contacts it after the lancet carrier has traveled least far. Angularly positioning the depth wheel 204 between the maximum-depth setting and the minimum-depth setting provides for one or a plurality of intermediate-depth settings. Optionally, the housing can include an indexing feature that engages cooperating indexing features of the depth wheel 204 (e.g., detents) to discretely define the depth settings.

In the depicted embodiment, the extension arm 83a extends longitudinally from the return-spring leg 83 and is integrally formed as a part thereof. As such, reference to the return-spring leg 83 includes the extension arm 83a, and vice versa. In some depth settings, the return contact surface 44 of the lancet carrier 32 may contact the extension arm 83a of the return-spring leg 83, and not just the remainder of the return-spring leg. Typically, both segments of the return spring 82 are made of the same resiliently deflectable material (e.g., metal or plastic), with the extension arm bent at an angle from the remainder of the return-spring leg 83. When the extension arm 83a hits the stop surface 216, generally it does not deflect (e.g., it may deflect but only insubstantially), so that position defines the extended position of the lancet carrier 32.

Having described in detail the structure of the lancing device 10 and its depth-adjustment mechanism 200, their sequential operation will now be described with particular reference to FIGS. 7-11. In a neutral position (FIG. 7), the leg 81 of the drive spring 80 and the leg 83 of the return spring 82 are engaged with their respective drive and return contact surfaces 42, 44 of the lancet carrier 32. Thus, the drive and return springs 80, 82 counter-balance one another such that the lancet carrier 32 generally remains in its neutral position. The pull-resist and push-resist equilibrium springs 100, 103 are typically in their neutral positions, or if charged in any respect they do not overpower the drive and return springs 80, 82 to significantly alter the position of the lancet carrier 32.

In a charged position (see FIG. 8), rearward/distal retraction (as indicated by the directional arrow) by a user of the push/pull button 94 has caused retraction of its foot portion 97 to retract the engaged thereby fin 78 of the lancet carrier 32. This retraction of the lancet carrier 32 has in turn caused retraction of the lancet-carrier drive contact surface 42 against the drive-spring leg 81 to charge the drive spring 80. At the same time, the return contact surface 44 of the lancet carrier 32 has been retracted away from engagement with the return spring 82. In the charged position, the barbs 58, 60 of the U-shaped portion 52 of the retracted lancet carrier 32 have releasably engaged the cooperating locking tabs 62, 64 of the housing 12 to retain the lancet carrier in the charged position. In addition, the pull-resist spring 103 has been charged by retraction of the push/pull button 94 to the charging position.

In a charged and ready position (see FIG. 9), the push/pull button 94 has been released by the user. Upon releasing the push/pull button 94, the charged pull-resist and push-resist equilibrium springs 100, 103 cause the push/pull button 94 to move proximally inward/forward to an equilibrium position (relative to the fully-retracted charged position of FIG. 8). As the push/pull button 94 translates proximally forward to its equilibrium position, the opening 24 in the housing 12 and the U-shaped portion 65 of the locking tab 64 (see FIG. 1) help guide the movement of the push/pull button and the leg 95 extending therefrom during discharging of the pull-resist and push-resist springs 100, 103.

To actuate the lancing device 10, the push/pull button 94 is now pressed by the user (as indicated by the directional arrow of FIG. 10). As the push/pull button 94 translates forward, its trigger posts 96, 98 come into engagement with the chamfered barbs 58, 60 of the arms 54, 56 of the lancet carrier 32 and deflect them inwardly. This releases the barbs 58, 60 from the retaining tabs 62, 64 of the housing 12 to release the lancet carrier 32 to be propelled through the lancing stroke under the influence of the charged drive spring 80. The engagement of the leg 81 of the charged drive spring 80 with the drive contact surface 41 of the lancet carrier 32 then propels the lancet carrier forward toward its extended position. As the lancet carrier 32 advances forward, its return contact surface 44 comes into contact with the leg 83 of the return spring 82 to begin charging the return spring. Because the drive spring 80 is stiffer than the return spring 82, the lancet carrier 32 continues moving forward under the influence of the discharging drive spring and against the influence of the charging return spring until it reaches its extended position.

The depth-adjustment mechanism 200 is adjustable between a series of depth settings to adjustably set the extended position of the lancet carrier 32. The momentum of lancet carrier 32 propelled forward by the drive spring 80 causes the leg 83 of the return spring 82 to angularly deflect (e.g., in a clockwise direction in the depicted views) from its neutral angular position (see FIG. 9) to charge the return spring. As the lancet carrier 32 continues translating forward, the extension arm 83a extending from the return-spring leg 83 transversely across the lancing stroke axis swings forward into contact with the eccentric stop surface 216 of the rotary depth dial 202. This engagement between the extension arm 83a of the return spring 82 and the eccentric stop surface 216 of the rotary depth dial 202 stops any further angular deflection of the return-spring leg 83. In turn, the engagement between the stopped return-spring leg 83 and the lancet-carrier return contact surface 44 stops any further forward movement of the lancet carrier 32. So this defines the extended position of the lancet carrier 32, which correlates to the extended-position deflection angle $\alpha 1$ (relative to its neutral position of FIG. 9) of the return-spring leg 83.

In this way, the lancet carrier 32 is not stopped at its extended position by contacting a fixed mechanical stop and thereby producing a "hard" stop. Instead, the lancet carrier 32 is stopped by contacting a resiliently deflectable spring leg 83 that is being deflected through an angular motion, with the spring-leg angular motion slowing down as the lancet carrier advances and stopped upon the spring leg contacting a fixed mechanical stop 216, and with the stopped spring-leg deflection thus stopping the forward motion of the lancet carrier. The resiliently deflectable spring leg 83 being operably interposed between the lancet carrier 32 and the mechanical stop 216 produces a "soft" (non-instant) stop. With this soft stop, there is less vibration produced and transmitted through the lancet to the patient, resulting in a less painful lancing experience for the patient.

The deflection angle of the return-spring leg 83 when the extension arm 83a has contacted and been stopped by the eccentric stop surface 216 of the rotary depth dial 202 determines the forward-most position of the lancet carrier 32 and thus determines the depth of penetration. For example, FIG. 10 shows the rotary wheel 204 of the depth dial 202 rotated to a position to provide a maximum depth of penetration of the lancet tip 34 (e.g., setting/indicia 4). In this position, the eccentric stop surface 216 of the depth dial 202 is correspondingly rotated to where its then-rearward facing portion in the engagement position is farthest forward to stop the forward motion of the extension arm 83a at a maximally advanced position, with the return-spring leg 83 at a maximally deflected angle $\alpha 1$. Accordingly, the depth-adjustment mechanism 200 is set to produce the maximally-extended extended position of the lancet carrier 32 and the lancet 30 it carries, i.e., to produce the deepest lancing penetration.

To highlight the adjustability feature, FIG. 11 shows the rotary wheel 204 of the depth dial 202 rotated to a position to provide a minimum depth of penetration (e.g., setting/indicia 1). In this position, the eccentric stop surface 216 of the depth dial 202 is correspondingly rotated to where its then-rearward facing portion in the engagement position is farthest rearward to stop the forward motion of the extension arm 83a at a minimally advanced position, with the return-spring leg 83 at a minimally deflected angle $\alpha 2$ (i.e., angle $\alpha 2$ is smaller than angle $\alpha 1$). Accordingly, the depth-adjustment mechanism 200 is set to produce the minimally-extended extended position of the lancet carrier 32 and the lancet 30 it carries, i.e., to produce the shallowest lancing penetration.

Upon the lancet carrier 32 reaching its extended position to puncture the skin (see FIG. 10), the now-charged return spring 82 then discharges to retract the lancet carrier to back within the housing 12. The lancet carrier 32 is then returned to the neutral position of FIG. 7, with the drive and return springs 80, 82 counter-balancing one another. The endcap 20 can be removed, the used lancet 30 removed, and a fresh lancet inserted into the lancet carrier 32 for use. This lancing procedure can then be repeated as desired.

Figure 12:
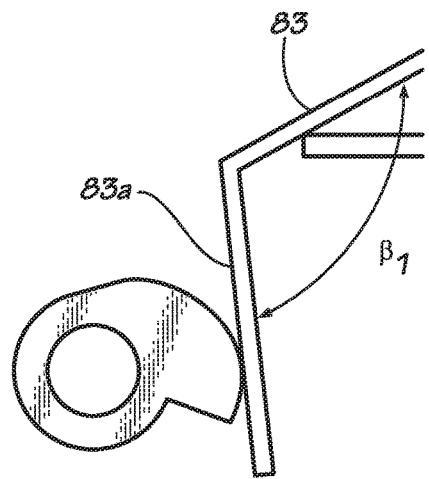
FIG. 12 is a top view of a portion of a depth-adjustment mechanism of a lancing device according to an alternative embodiment, showing the lancet carrier approaching an extended position.
Figure 13:
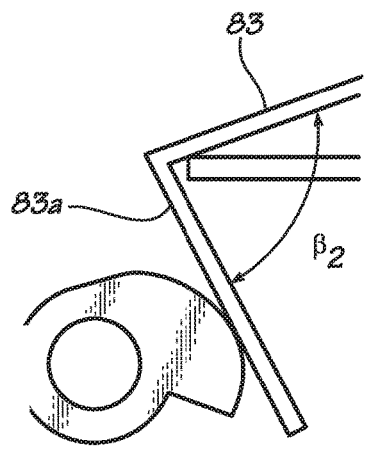
FIG. 13 shows the portion of a depth-adjustment mechanism of FIG. 12, with the lancet carrier in the extended position.

In an alternative embodiment shown in FIGS. 12-13, the extension arm 83a is resiliently deflectable (with respect to the return-spring leg 83) so that its contact with the eccentric stop surface 216 of the depth dial 202 provides for an even "softer" stop with less vibration sensed by the patient being lanced. This is because the angle between the extension arm 83a and the return-spring leg 83 smoothly and progressively decreases from a neutral angle $\beta 1$ (see FIG. 12) to a deflected angle $\beta 2$ (see FIG. 13) where the lancet carrier 32 is stopped at the extended position. In such embodiments, the extension arm 83a may have a different (e.g., stiffer) spring stiffness and/or be connected to the remainder of the return-spring leg 83 by a resiliently deflectable junction.

Figure 14:
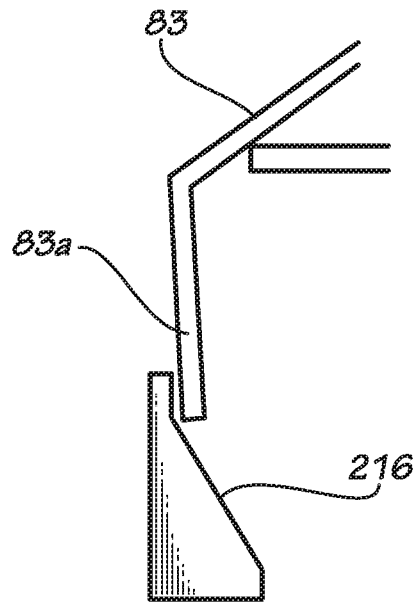
FIG. 14 is a top view of a portion of a depth-adjustment mechanism of a lancing device according to another alternative embodiment, adjusted to a maximally extended position.
Figure 15:
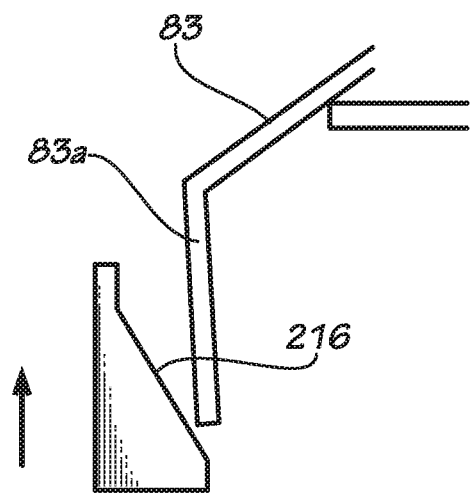
FIG. 15 shows the portion of a depth-adjustment mechanism of FIG. 14 adjusted to a minimally extended position.

In another alternative embodiment shown in FIGS. 14-15, the adjustably-positioned stop surface is formed by a ramp 216 that is linearly slidable to position different-thickness portions of it for engagement by the extension arm 83a. The ramp 216 slides between a maximally extended position (see FIG. 14) and a minimally extended position (see FIG. 15).

In other embodiments, the resiliently deflectable extension arm extends from the movable adjustment control member (not the return-spring leg) and engages the return-spring leg to stop forward motion of the lancet. In yet other embodiments, the resiliently deflectable extension arm engaged by the lancet carrier is not part of the return spring but instead is provided as a separate spring element. In still other embodiments, the extension arm is a resiliently deflectable extension arm cantilevered from the lancet carrier (or another element that moves with the lancet), but is not an extension of or otherwise a part of the return spring.

And in some embodiments, the lancing device is provided with the soft-stop features (the resiliently deflectable extension arm engaging the stop surface) but not the adjustability features (the stop surface being eccentric and rotationally moveable). In such embodiments, the soft-stop mechanism includes the resiliently deflectable leg operably interposed between the lancet carrier and the stop surface to produce the non-instant stop of the lancet carrier at the extended position to reduce vibration for a less painful lancing experience. But the stop surface is fixed and not adjustable, so it includes only one portion that is contacted in the engagement position by the resiliently deflectable leg, and it does not include the rotary wheel or any other adjustable control member.

While the invention has been described with reference to example embodiments, it will be understood by those skilled in the art that a variety of modifications, additions, and deletions are inherently and implicitly within the scope of the invention, as defined by the following claims.

What is claimed is:

1. A lancing device for propelling a lancet through a lancing stroke, the lancing device comprising:
   a housing including an axial bore;
   a drive mechanism including a lancet carrier and a drive spring, the lancet carrier holding the lancet and translatable axially within the housing bore through the lancing stroke, and the drive spring adapted to propel the lancet carrier through a forward phase of the lancing stroke; and
   a depth-adjustment mechanism including an adjustably positioned stop surface, a movable adjustment control member operably coupled thereto, and a resiliently deflectable leg operably interposed between the lancet carrier and the stop surface, wherein the lancet carrier engages and deflects the leg in the forward phase of the lancing stroke, and the deflecting leg then engages the stop surface to stop the leg deflection and thus stop the forward motion of the lancet carrier at an extended position for lancing, and wherein the control member is adjustably positionable to move different portions of the stop surface into an engagement position where they are contacted by the leg to adjust the extended position and thereby adjust a penetration depth of the lancet;
   wherein the drive mechanism includes a return spring adapted to contact and be charged by the lancet carrier during the forward phase of the lancing stroke and then discharge and retract the lancet carrier from the extended position, wherein the return spring includes the resiliently deflectable leg; and
   wherein the return spring is a torsion spring.

2. The lancing device of claim 1, wherein the resiliently deflectable leg being operably interposed between the lancet carrier and the stop surface produces a non-instant stop of the lancet carrier at the extended position to reduce vibration for a less painful lancing experience.

3. The lancing device of claim 1, wherein the lancet carrier defines a return contact surface that engages the resiliently deflectable leg.

4. The lancing device of claim 1, wherein the return-spring leg includes an extension arm that contacts the stop surface in the lancet-carrier extended position.

5. The lancing device of claim 4, wherein the extension arm is angled with respect to the return-spring leg and extends transversely across an axis defined by the lancing stroke.

6. The lancing device of claim 5, wherein the extension arm angularly deflects relative to the remainder of the leg upon contact with the stop surface.

7. The lancing device of claim 1, wherein the adjustably positioned stop surface is defined by an eccentric stop surface of a rotary shaft rotationally mounted to the housing.

8. The lancing device of claim 7, wherein the rotary shaft is rotationally adjustable to place the different portions of the eccentric stop surface in the engagement position where they are contacted by the leg to adjust the extended position and thereby adjust the penetration depth of the lancet.

9. The lancing device of claim 7, wherein the different portions of the eccentric stop surface have different radial dimensions.

10. The lancing device of claim 7, wherein the movable control member is a rotary wheel from which the rotary shaft axially extends, with the rotary wheel accessible by a user to permit rotational movement thereof to adjust the portion of the eccentric stop surface in the engagement position and thereby adjust the penetration depth of the lancet.

11. The lancing device of claim 10, wherein the rotary wheel includes indicia corresponding to the different portions of the eccentric stop surface.

12. A depth-adjustment mechanism for a lancing device, the lancing device comprising a lancet carrier holding a lancet and translatable axially through a lancing stroke, a drive spring adapted to propel the lancet carrier through a forward phase of the lancing stroke to an extended position for lancing, and a return spring adapted to retract the lancet carrier from the extended position, the depth-adjustment mechanism comprising:

an adjustably positioned stop surface;
a movable adjustment control member operably coupled to the stop surface; and
a resiliently deflectable leg formed by the return spring and including an extension arm attached to the distal end of the deflectable leg, the extension arm extending transversely across an axis defined by the lancing stroke, contacting the stop surface in the lancet-carrier extended position, and operably interposed between the lancet carrier and the stop surface,
wherein the lancet carrier engages and deflects the deflectable leg in the forward phase of the lancing stroke, and the extension arm then engages the stop surface to stop the extension-arm and deflectable leg deflection and thus stop the forward motion of the lancet carrier at the extended position, wherein the extension arm being operably interposed between the lancet carrier and the stop surface produces a non-instant stop of the lancet carrier at the extended position to reduce vibration for a less painful lancing experience, and wherein the control member is adjustably positionable to move different portions of the stop surface into an engagement position where they are contacted by the extension arm to adjust the extended position and thereby adjust a penetration depth of the lancet;
wherein the return spring is a torsion spring.

13. The lancing device of claim 12, wherein the adjustably positioned stop surface is defined by an eccentric stop surface of a rotary shaft rotationally mounted to the housing.

14. The lancing device of claim 13, wherein the rotary shaft is rotationally adjustable to place the different portions of the eccentric stop surface in the engagement position where they are contacted by the leg to adjust the extended position and thereby adjust the penetration depth of the lancet, wherein the different portions of the eccentric stop surface have different radial dimensions.

* * * * *